United States Patent [19]

Gabbay et al.

[11] 4,268,270

[45] May 19, 1981

[54] GLYCOSYLATED HEMOGLOBIN MEASUREMENT

[75] Inventors: Kenneth H. Gabbay; Paul M. Gallop, both of Chestnut Hill, Mass.

[73] Assignee: Children's Hospital Medical Center, Boston, Mass.

[21] Appl. No.: 34,755

[22] Filed: Apr. 30, 1979

[51] Int. Cl.³ .................... G01N 33/52; G01N 33/66; G01N 33/72; G01N 33/58

[52] U.S. Cl. .............................. 23/230.3; 23/230 B; 23/901; 23/913; 252/408; 422/58; 422/59; 422/61; 422/68; 424/1

[58] Field of Search ................... 23/230 B, 230.3, 901, 23/913; 252/408; 422/61, 58, 59, 68

[56] References Cited

U.S. PATENT DOCUMENTS 4,142,855 3/1979 Acuff ................................ 23/230 B

FOREIGN PATENT DOCUMENTS 1293903 10/1972 United Kingdom .

OTHER PUBLICATIONS

S. Rahbar, Clin. Chim. Acta, 22, 296-298 (1968).
L. A. Trivelli et al., N. Eng. J. Med., 284, pp. 353-357 (1971).
H. Franklin Bunn et al., J. Clin. Invest., 57, pp. 1652-1659 (Jun. 1976).
R. Fluckiger et al., FEBS Letters, 71(2), pp. 356-360 (Dec. 1976).
H. Franklin Bunn et al., Biochem and Biophys, Research Communications, 67(1), pp. 103-109 (1975).
H. Franklin Bunn et al., Science, 200, pp. 21-27 (Apr. 1978).
Chemical Abstracts, 69:49194c (1968).
H. Franklin Bunn et al., paper entitled "Structural Heterogeneity of Human Hemoglobin", Presented in Part of the American Society of Biological Chemists, Jun. 1978.
K. H. Gabbay et al., J. Clin. Endocrinology and Metabolism, 44(5), pp. 859-864 (May 1977).
Y. Massamiri et al., Anal. Biochem, 91, pp. 618-625 (1978).
K. H. Gabbay et al., paper entitled "Glycoslated Hemoglobins: Increased Glycosylation of Hemoglobin A in Diabetic Patients", Presented in Part at Annual Meeting of the American Society for Clinical Investigation, San Francisco, Calif., May 1, 1978.

Primary Examiner—Sidney Marantz

[57] ABSTRACT

Process and apparatus for measuring glycosylated hemoglobin by assaying bound glyco groups in hemolysate featuring, in one aspect, appropriate oxidation of glycosylated hemoglobin and the rapid measurement of the resultant aldehydic compounds.

40 Claims, 5 Drawing Figures

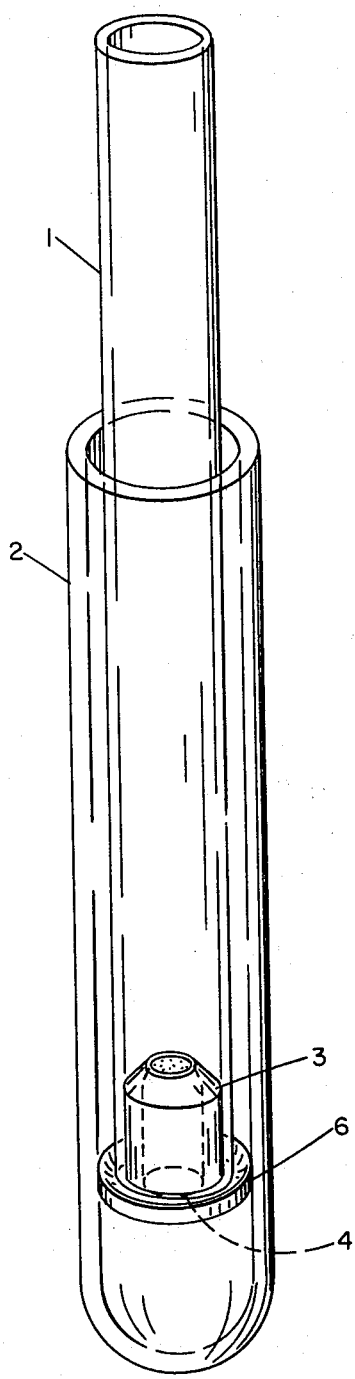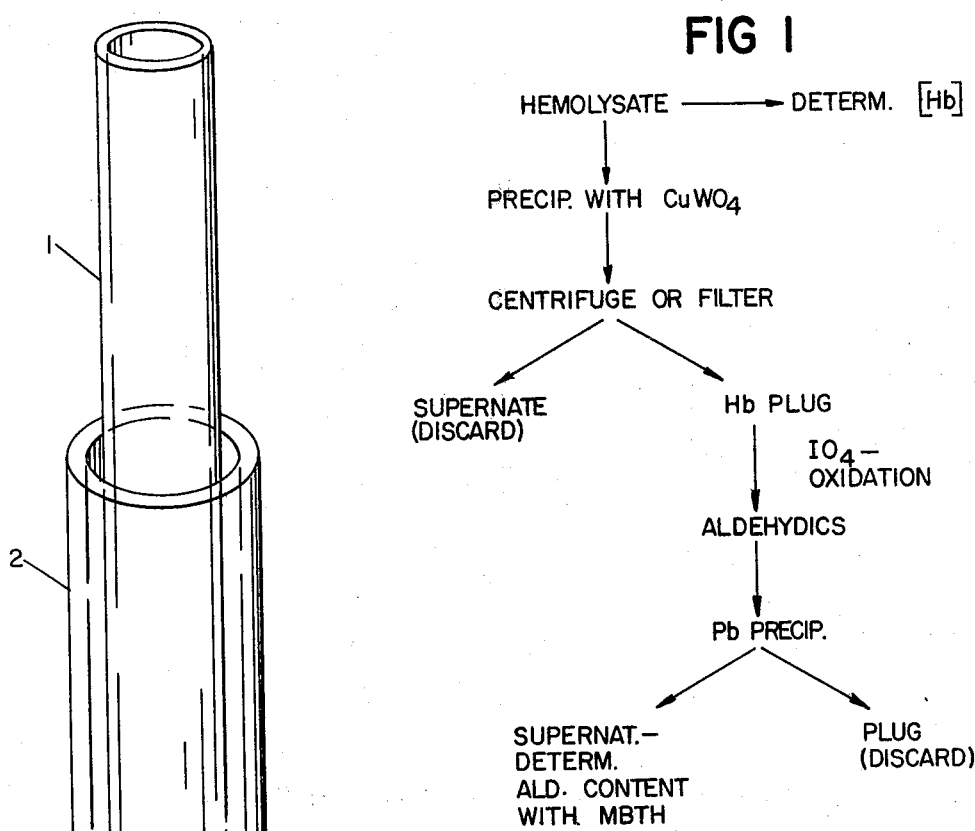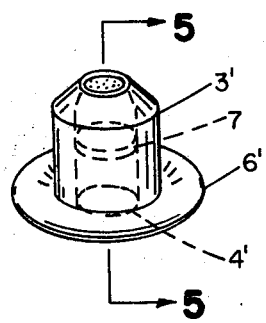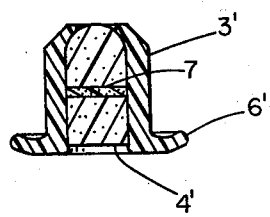

GLYCOSYLATED HEMOGLOBIN MEASUREMENT

FIELD OF THE INVENTION

This invention relates to measurement of long-term average blood sugar levels.

BACKGROUND OF THE INVENTION

In measuring blood sugar levels, it is desirable to employ a method which accurately reflects the average long-term level rather than short-term fluctuations; the method should be simple and economical. Since soluble blood sugar levels can exhibit extensive short-term fluctuations in both diabetics and in normal subjects, other measures of blood sugar levels have been investigated. One such alternative measure is the hemoglobin fraction termed $HbA_{1c}$. This minor fraction is formed by a slow non-enzymatic condensation of glucose with the N-terminal amino group of the $\beta$ chain of $HbA_0$, the main hemoglobin component. The observation made by Rahbar (1968) Clin. Chim. Acta 22:296-298; Trivelli et al. (1971) N. Engl. J. Med. 284, 353-357; and Gabbay et al. (1977) J. Clin. Endocrinal. Metab. 44, 859-864, that the $HbA_{1c}$ fraction is elevated 2-3 fold in patients suffering from diabetes mellitus has led to the use of measurement of the $HbA_{1c}$ fraction by ion exchange column techniques as a diagnostic tool to follow diabetic control.

Another method of quantifying the $A_{1c}$ fraction has been described in Flückiger et al. (1976) FEBS-Lett. 71:356-360. Glycosylation of the hemoglobin fraction at sites other than the amino terminal position of a hemoglobin chain is quantified by heating the protein under acidic conditions and colorimetrically measuring the generated furfural compounds with 2-thiobarbituric acid.

SUMMARY OF THE INVENTION

Our invention provides a method and apparatus for accurately and simply measuring the level of glycosylated hemoglobin. The invention takes advantage of the fact that a hexose bonded to the various amino groups of hemoglobin chains releases aldehydic compounds when the glycosylated hemoglobin is appropriately oxidized.

In one aspect, the invention features measuring glycosylation by oxidizing a hemoglobin sample and measuring the quantity of generated aldehydic compounds.

In some preferred embodiments the hemoglobin sample can be reduced prior to oxidation so that the bound and now reduced hexose linkage can generate an additional aldehydic compound upon appropriate oxidation; the hemoglobin is immobilized and separated from soluble sugars prior to appropriate oxidation either by precipitation or by selective binding to a resin. Depending on the variation selected, the immobilized hemoglobin may or may not be resolubilized prior to oxidation; and finally, the aldehydic compounds generated by the appropriate oxidation are measured colorometrically.

In other preferred embodiments red cells are washed with normal saline to remove soluble sugars; the cells are lysed in distilled water; the hemolysate is centrifuged; the glycosylated hemoglobin is reduced and appropriately oxidized; and finally, the aldehydic compounds generated by the appropriate oxidation are measured colorimetrically.

In another aspect, the invention features immersing a known amount of haptoglobin in hemolysate to bind a predictable amount of hemoglobin, and measuring the glycosylated hemoglobin content. In a preferred embodiment, glycosylated hemoglobin content is determined by immersing the haptoglobin-bound hemoglobin sample in a tritiated reducing compound, and then measuring the radioactivity level of the sample.

The invention makes possible measuring the level of glycosylated hemoglobin quickly and simply within one reaction vessel.

DESCRIPTION OF THE PREFERRED EMBODIMENT

We turn now to the description of preferred embodiments and their operation, after first briefly describing the drawings.

DRAWINGS

FIGS. 1 and 2 are flow diagrams for alternate methods of assaying glyco group equivalents in hemoglobin.

FIG. 3 is a perspective view of apparatus for carrying out such methods.

FIG. 4 is a perspective view of a plug employed in a preferred embodiment of the invention, showing different filters.

FIG. 5 is a sectional view of the plug of FIG. 3 taken along line 4—4.

EMBODIMENTS

Figure 2:
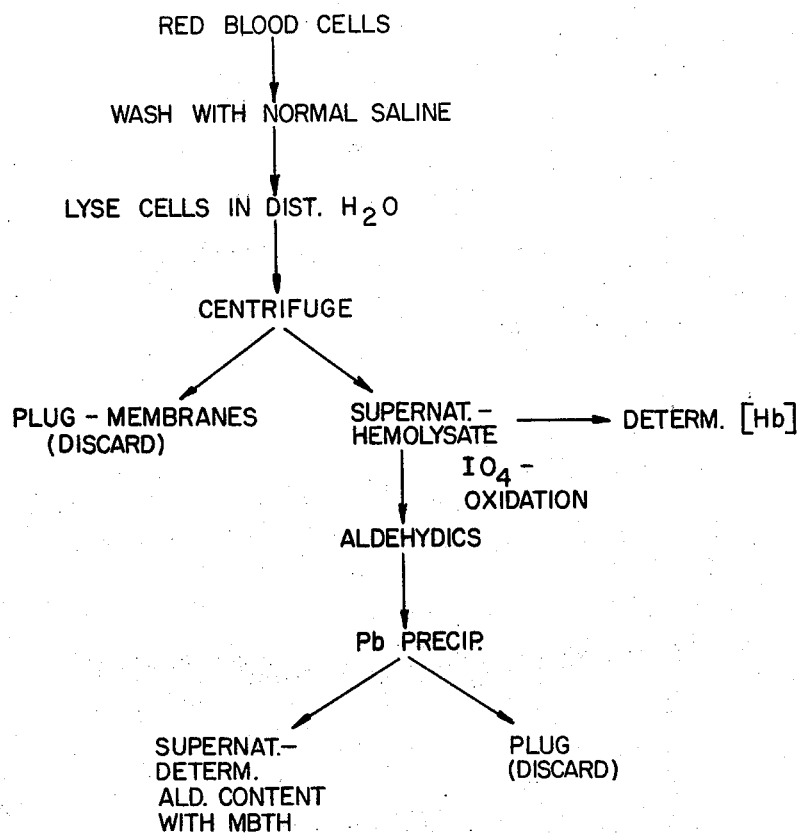

There is shown in FIG. 1 a flow diagram for one method of assaying glyco group equivalents in hemoglobin. Whole blood is centrifuged and the red cells are washed twice with normal saline (0.9% NaCl). The cells are suspended in 6 volumes of distilled water and allowed to lyse for two minutes. Buffer is added and the hemolysate is then centrifuged at 18,000 rpm for 30 minutes to remove red cell membranes.

Aliquots of 100 μl samples of spun hemolysate, each containing 2.5-3.5 mg hemoglobin, are placed in test tubes in duplicate. A blank without hemolysate is also run. Hemoglobin concentration is determined in the usual manner using additional 100 μl aliquots mixed with 5.0 ml Drabkin's solution (0.20 g $K_3Fe(CN)_6$, 0.05 g KCN, and 1.00 g $NaHCO_3$ made up to 1 l with distilled water). Absorbance of these aliquots is measured at 540 nm against Drabkin's solution to calculate hemoglobin concentration.

To precipitate the hemoglobin in the assay samples, 1.0 ml of 0.5% $CuSO_4.5H_2O$ and 100 μl of 0.75% $Na_2WO_4.2H_2O$ are added to and mixed with each sample. After 1 minute the sample tubes are centrifuged for 2 minutes at 2500 rpm and the supernatants, containing soluble sugars (sugars not bound to hemoglobin) are discarded. Filtration may be used instead of centrifugation to remove soluble sugars.

At this point the hemoglobin plug may be directly oxidized with periodate, as shown in FIG. 1, or it may be resolubilized first. Direct oxidation of the hemoglobin precipitate is simple but has the disadvantage of being a heterogeneous reaction in which complete hemoglobin oxidation takes slightly longer. Solubilization of the plug in an acid such as HCl prior to oxidation allows the faster oxidation characteristic of a homogenous reaction, although both approaches work well.

Oxidation is performed either by suspending the finely divided hemoglobin plugs in 0.5 ml of 0.02 M $NaIO_4$ (periodate) or by adding periodate to the hemoglobin in solution. After this step, the remaining steps for solubilized and unsolubilized hemoglobin are the same. After 15 minutes of frequent vortex mixing, 100 µl of 0.25 M $Pb(NO_3)_2$ titrated to pH 8 with sodium acetate is added to stop the reaction and to precipitate the excess periodate and iodate products, since they interfere with the colorometric test. The tubes are then centrifuged for 2 minutes, or the contents filtered; the supernatant containing the aldehydes is clear and ready for colorometric analysis.

To determine aldehyde content colorimetrically, aliquots of 500 µl of the clear supernatant in new test tubes are mixed and incubated for 10 minutes with 100 µl of filtered 1% (w/v in aqueous solution) 3-methyl-2-benzothiazolinone hydrazone hydrochloride monohydrate (MBTH) which has been stored at 4° C. for not more than 10 days. Next, 1.00 ml of 0.40% $FeCl_3.6H_2O$ is added and after 5 minutes, 3.00 ml of reagent grade acetone is added rapidly with mixing to stop the reaction. Absorbance, which is directly proportional to aldehyde content after oxidation, and therefore to glyco group equivalents before oxidation, is measured at 670 nm against the no-hemoglobin blank.

Duplicates are averaged, and absorbance (optical density) is calculated as follows:

$$OD_{670}/mg\ Hb = \frac{(avg\ OD_{670})}{(avg\ OD_{540})(1.47\ mg/ml/OD_{540})(0.1\ ml)(51)}$$

$$= \frac{(OD_{670})}{(OD_{540})(7.50)}$$

Absorbance is converted to glyco group equivalents per ml hemoglobin by colorometrically analyzing samples simultaneously with standards which have been calibrated by a method such as the $[^3H]$-$NaBH_4$ reduction method described in Bookchin and Gallop (1968) Biochem. Biophys. Res. Comm., 32:86. Alternatively, sorbitol or fructose can be used as standards. These standards, containing a range of sugar levels, provide a standard curve on which sample values are plotted.

In variations of the above the hemoglobin in the hemolysate may be immobilized and separated from soluble sugars by binding it to a cation exchange resin such as Biorex-70 (Biorad), CG-50 (Rohm & Haas), or Dowex-50 (Dow), rather than precipitating it with $CuOS_4$ and $Na_2WO_4$. The remaining steps are essentially the same as described.

The sensitivity of any variation of the above-described method may be enhanced by initially reducing the glycosylated hemoglobin with $NaBH_4$ prior to oxidation, making an additional hydroxyl group of the bound hexose available for aldehyde formation upon oxidation. The hemoglobin is treated with a 100-fold molar excess of $NaBH_4$ in phosphate buffer, pH 7.5, for one hour at room temperature. Excess $NaBH_4$ is removed from the reduced hemoglobin by centrifugation or filtration.

There is shown in FIG. 2 a flow diagram for another variation of the above-described method of assaying glyco group equivalents in hemoglobin; the chief difference is the absence of a hemoglobin immobilization step in the FIG. 2 variation. Oxidation is performed more efficiently using this variation because the hemoglobin is in solution when the periodate is added.

Whole blood is washed three times with normal saline; this washing removes most soluble sugars. The cells are suspended in 6 volumes of distilled water and allowed to lyse for two minutes. 0.5 M phosphate buffer, pH 6.8 is added to make 0.05 M phosphate and the hemolysate is then centrifuged at 18,000 rpm for 30 minutes to remove red cell membranes.

If desired, reduction of the glycosylated hemoglobin is accomplished by adding 0.1 ml of $NaBH_4$ (at a concentration of 5 mg/ml) to 0.1 ml of hemolysate and incubating for ten minutes. The reaction is stopped by adding 0.7 ml of 0.036 M phosphoric acid.

If the glycosylated hemoglobin has not been reduced, 0.6 ml of distilled water is added to a 0.1 ml hemoglobin sample prior to oxidation. Appropriate oxidation is accomplished by adding to the sample 0.1 ml of 0.2 M sodium periodate and incubating for 15 minutes at room temperature. Then 0.3 ml of 0.38 M $PbNO_3$ (untitrated) is added, followed by the addition of 0.1 ml of 1.4 M NaOH. The precipitate is removed by filtering or centrifuging for 2 minutes.

To 1.0 ml of clear supernatant containing aldehydes is added 0.1 ml of 1% MBTH. After 10 minutes of incubation at room temperature, 0.5 ml of 0.8% ferric chloride is added and allowed to incubate for 5 minutes at room temperature. Finally, 3 ml of distilled water is added with rapid mixing. Absorbance and glyco group equivalents per ml hemoglobin are determined as previously described.

Apparatus useful in practice of the invention is illustrated in FIG. 3. The apparatus employs the method for hemoglobin-bound glyco group determination herein disclosed. The rim 6 of plug 3 fits snugly but movably within outer test tube 2. Plug 3, whose inner core contains filter 4, fits immovably in the end of inner tube 1.

In one type of operation, the bottom of tube 2 contains a cation exchange resin which is capable of binding hemoglobin. Tube 1 contains 100 µl of hemolysate of known hemoglobin concentration in 0.05 M sodium phosphate buffer. Tube 1 is pulled upward to allow the hemolysate and buffer to pass downward through filter 4 to the resin. After a few minutes the hemoglobin binds to the resin and tube 1 is pushed down. Unbound material, including sugars in solution, passes up through filter 4 and is discarded. Next 0.5 ml of 0.02 M $NaIO_4$ is introduced into tube 1, which is then pulled up to allow the $NaIO_4$ to pass through filter 4 into the bottom of tube 2 with the resin-bound hemoglobin.

While the oxidation reaction is proceeding, tube 1 is pulled all the way out of tube 2, and plug 3 is replaced with plug 3', shown in FIGS. 4 and 5. Plug 3' is similar to plug 3 of FIG. 3, but contains a section of fine glass wool 7.

After oxidation has been completed, 100 µl of 0.25 M $Pb(NO_3)_2$ which has been titrated to pH 8 with anhydrous sodium acetate, is added to the contents of tube 2 to precipitate excess $IO_3^-$ and $IO_4^-$ products. Tube 1, equipped with plug 3', is reinserted into tube 2 and pushed down to allow the supernatant, which contains the aldehydic products to be measured, to pass up through filters 4 and 7. The supernatant is mixed with 1% MBTH, incubated for 10 minutes, then analyzed color metrically as previously described.

Instead of a cation exchange resin to bind hemoglobin, $CuWO_4$ can be employed to precipitate hemoglobin, using a modification of the apparatus shown in FIG. 3, that modification being a finer filter 4. In tube 2, 100 µl of hemolysate of known hemoglobin concentration in buffer (prepared as previously described), is mixed with 1.0 ml of $CuSO_4.5H_2O$ and 100 μl of 0.75% $Na_2WO_4.2H_2O$ to precipitate the hemoglobin. Tube 1 is then inserted into tube 2 and pushed down to allow unprecipitated material to pass upward through fine filter 4 so it can be discarded. The remaining steps are the same as those described in connection with the first-described apparatus embodiment.

The operation of the apparatus embodiment employing copper tungstate can be modified by adding the step of resolubilizing the tungstate-hemoglobin precipitate with HCl prior to oxidation. The HCl is added to tube 1 after the unprecipitated material has been discarded and tube 1 is pulled up to allow the HCl to pass down through filter 4 into the tungstenate-hemoglobin precipitate. This added step provides for a more complete homogeneous oxidation reaction.

The operation of the embodiments described above may be further modified by, as a first step, hemolyzing whole blood in tube 2 with normal saline followed by distilled water. Also, the sensitivity of the tests described in connection with the kits can be enhanced by adding, between the steps of hemoglobin immobilization and periodate oxidation, the step of reducing the glycosylated hemoglobin with $NaBH_4$. A 100-fold molar excess of $NaBH_4$ is added to tube 1, which is pulled up to allow the $NaBH_4$ to pass downward through filter 4 so it can reduce the glycosylated hemoglobin in the bottom of tube 2.

The apparatus shown in FIG. 3 may also be employed in conjunction with the previously-described method (shown in FIG. 2) in which the hemoglobin is not immobilized prior to oxidation. The reagents are the same as in the previously-described method, and the apparatus is used generally as described above, with appropriate modifications.

Another embodiment of the invention employs haptoglobin binding. A glass rod coated with a known quantity of haptoglobin beads is dipped into red cell hemolysate so that a predictable amount of representative hemoglobin (glycosylated and unglycoslyated) is fished out, bound to the haptoglobin. (One molecule of haptoglobin binds one molecule of hemoglobin.) The resulting support-hemoglobin adduct (SHA) is washed by immersion in saline, then dipped into calibrated [$^3$H]-$NaBH_4$ solution, thereby specifically reducing and labelling the hemoglobin-bound glyco groups. The SHA is washed and then counted in a scintillation counter. This method is accurate and eliminates the need for measuring the amount of hemoglobin in the samples; it is thus a method susceptible to automation. Another advantage of this method is that the washing step need not include special procedures for preventing the loss of any of the hemoglobin sample, since the haptoglobinhemoglobin complex remains firmly fixed on the support throughout the analysis.

OTHER EMBODIMENTS

Other embodiments of the invention are within the following claims. For example, hemoglobin can be separated from soluble blood sugar using dialysis or sizing columns. Excess periodate products can be removed using ion exchange resins such as Dowex-1 rather than a precipitating agent. These products can also be removed using rapid dialysis, a method which lends itself to automation. Moreover, the entire method can be automated e.g., using continuous flow or discrete analysis equipment. Oxidation can be performed using any salt of periodic acid, or with other substances such as lead tetraacetate. Gas chromatography rather than colorometric analysis can be used to measure formaldehyde (the major aldehydic product); this method obviates removal of excess periodate. Aldehydic compounds can also be measured enzymatically. The colorometric analysis can be performed using, e.g., a compound such as chromotropic acid rather than MBTH, though MBTH is preferred for simplicity and sensitivity.

What is claimed is:
1. In the process of measuring glycosylated hemoglobin, the steps comprising:
   providing a sample containing hemoglobin including an unknown quantity of glycosylated hemoglobin,
   oxidizing said glycosylated hemoglobin thereby to generate aldehydic compounds, and
   determining the quantity of aldehydic compounds so generated, said quantity of aldehydic compounds being directly proportional to said unknown quantity of glycosylated hemoglobin.
2. The process of claim 1 wherein said oxidizing is performed by reacting said glycosylated hemoglobin with a salt of periodic acid.
3. The process of claim 1 wherein said quantity of aldehydic compounds is determined colorometrically.
4. The process of claim 1 further comprising the step of reducing said glycosylated hemoglobin with a reducing agent prior to said oxidizing, whereby said quantity of aldehydic compounds generated by said oxidation is increased.
5. The process of claim 4 wherein said reducing agent consists of $NaBH_4$.
6. The process of claim 1 further comprising the step of separating sugars not bound to hemoglobin from the hemoglobin in said sample, prior to said oxidizing.
7. The process of claim 6 wherein said separating comprises binding said hemoglobin to a cation exchange resin.
8. The process of claim 6 wherein said separating comprises precipitating said hemoglobin.
9. The process of claim 8 wherein said precipitating comprises reacting said hemoglobin with $CuSO_4$ and $Na_2WO_4$.
10. The process of claim 6 or claim 7 further comprising the step of resolubilizing said hemoglobin prior to said oxidizing.
11. The process of claim 10 wherein said step of resolubilizing said hemoglobin comprises dissolving said hemoglobin in HCl.
12. The process of claim 6 wherein said separating comprises washing red blood cells with normal saline.
13. The process of claim 12 further comprising the step of reducing said glycosylated hemoglobin with $NaBH_4$ prior to said oxidizing, whereby said quantity of aldehydic compounds generated by said oxidation is increased.
14. The process of claim 13 wherein said step of reducing said glycosylated hemoglobin is completed by the addition of acid, whereby said reducing is stopped.
15. In the process of measuring glycosylated hemoglobin, that improvement comprising:
   obtaining a hemoglobin sample of known size by immersing a known amount of haptoglobin in a red cell hemolysate, thereby to bind thereon said hemoglobin sample of known size, and
   thereafter determining the glycosylated hemoglobin content of said hemoglobin sample.

16. The process of claim 15 wherein said step of determining the glycosylated hemoglobin content of said hemoglobin sample comprises the steps of:
  immersing said hemoglobin sample in a tritiated reducing compound, therby radioactively labelling the hemoglobin-bound glyco groups, and
  measuring the radioactivity level of said hemoglobin sample, said radioactivity level being directly proportional to said glycosylated hemoglobin content of said hemoglobin sample.

17. The process of claim 16 wherein said tritiated reducing compound consists of [$^3$H]-NaBH$_4$.

18. A combination of test equipment and reagents for measuring glycosylated hemoglobin, comprising in combination
  a container for receiving a liquid sample containing hemoglobin including an unknown quantity of glycosylated hemoglobin,
  a first chemical reagent selected to oxidize said glycosylated hemoglobin upon addition to said container containing said sample, to generate aldehydic compounds in said container, and
  a second chemical reagent selected to react with said aldehydic compounds upon addition to said container to produce products having a measurable characteristic uniquely distinctive of said unknown quantity.

19. The combination of claim 18 further comprising a measuring standard against which said characteristic can be measured to determine said unknown quantity.

20. The combination of claim 19 wherein said standard is a colormetric standard.

21. The apparatus of claim 18 wherein said second reagent comprises means to produce said products wherein said measurable characteristic is optical density, for colorometric determination of said unknown quantity.

22. The apparatus of claim 21 wherein said second reagent comprises 3-methyl-2-benzothiazolinone hydrazone hydrochloride monohydrate.

23. The apparatus of claim 22 wherein said means for colorometric analysis further comprises ferric chloride.

24. The apparatus of claim 21, further comprising:
  means for separating hemoglobin from soluble sugars,
  means for removing excess IO$_3$ and IO$_4$ products, and
  means for stopping the action of said second reagent.

25. The apparatus of claim 24 wherein said means for separating hemoglobin from soluble sugars consists of a cation exchange resin.

26. The apparatus of claim 24 wherein said means for removing excess IO$_3$ and IO$_4$ comprises a rapid dialyzer.

27. The apparatus of claim 24 wherein said means for separating hemoglobin from soluble sugars consists of normal saline.

28. The apparatus of claim 24 wherein said means for separating hemoglobin from soluble sugars consists of chemical solution means which combines with hemoglobin to form an insoluble precipitate.

29. The apparatus of claim 28 wherein said chemical solution means consists of CuSO$_4$ and Na$_2$WO$_4$ in aqueous solutions.

30. The apparatus of claim 24 further comprising means for resolubilizing said immobilized hemoglobin.

31. The apparatus of claim 30 wherein said means for resolubilizing said immobilized hemoglobin consists of HCl.

32. The apparatus of claim 24 wherein said means for removing excess IO$_3^-$ and IO$_4^-$ consists of a chemical compound which combines with IO$_3^-$ and IO$_4^-$ to form an insoluble precipitate.

33. The apparatus of claim 32 wherein said chemical compound consists of Pb (NO$_3$)$_2$.

34. The apparatus of claim 32 wherein said chemical compound consists of lead acetate.

35. The apparatus of claim 24 further comprising means for reducing said hemoglobin prior to oxidation.

36. The apparatus of claim 35 wherein said means for reducing said hemoglobin prior to oxidation consists of NaBH$_4$.

37. The apparatus of claim 36 further comprising means for stopping the action of said NaBH$_4$.

38. The apparatus of claim 37 wherein said means for stopping said action of said NaBH$_4$ consists of phosphoric acid.

39. Test equipment and reagent means for measuring glycosylated hemoglobin in a sample comprising, in combination
  a solid support coated with a predetermined quantity of haptoglobin capable of binding a molar equivalent of hemoglobin, and
  a chemical reagent capable of reacting with any glycol groups attached to said haptoglobin-bound hemoglobin to generate measurable products.

40. The combination of claim 39 wherein said chemical reagent capable of reacting with said glycol groups is [$^3$H]-NaBH$_4$.

* * * * *